United States Patent [19]

Grüninger et al.

[11] Patent Number: 5,432,069

[45] Date of Patent: Jul. 11, 1995

[54] **TOCOPHEROL CYCLASE ISOLATED FROM *CHLORELLA PROTOTHECOIDES, DUNALIELLA SALINA* AND WHEAT LEAVES**

[75] Inventors: Fiona Grüninger, Arlesheim, Switzerland; Erich Hochuli, Montclair, N.J.; Peter K. Matzinger, Rodersdorf, Switzerland

[73] Assignee: Hoffmann-La Roche Inc., Nutley, N.J.

[21] Appl. No.: 916,235

[22] Filed: Jul. 17, 1992

[30] Foreign Application Priority Data

Jul. 18, 1991 [EP] European Pat. Off. ........... 91112006
Jun. 26, 1992 [EP] European Pat. Off. ........... 92110874

[51] Int. Cl.$^6$ ................ C12N 9/00; C12P 17/06; C12P 7/00; C12P 7/22
[52] U.S. Cl. .................... 435/183; 435/125; 435/132; 435/156
[58] Field of Search ............. 435/183, 125, 132, 156

[56] References Cited

U.S. PATENT DOCUMENTS

| | | | |
|---|---|---|---|
| 2,640,058 | 5/1953 | Weisler | 549/408 |
| 3,819,657 | 6/1974 | Baldwin et al. | 549/412 |
| 4,115,949 | 9/1978 | Avron et al. | 568/869 |
| 4,554,390 | 11/1985 | Curtain et al. | 568/869 |
| 4,582,919 | 4/1986 | Barner et al. | 549/554 |
| 4,709,055 | 11/1987 | Barner et al. | 549/215 |
| 4,958,460 | 9/1990 | Nielson et al. | 47/1.4 |

FOREIGN PATENT DOCUMENTS

| | | |
|---|---|---|
| 058945 | 2/1982 | European Pat. Off. |
| 90/01554 | 2/1990 | WIPO |

OTHER PUBLICATIONS

Henry et al., "Intermediates of Tocopherol biosynthesis in the Unicellulor alga Scenedesmus obliquus", Biochem. J. 242, 367–373, 1987.

Dasilva et al., "Content of α-Tocopherol in some Blue-green algae", Biochimica et Biophysica Acta, vol. 239, 1971pp. 345–347.

Whistance et al., "Biosynthesis of Phytoquinones", Biochemical Journal, vol. 117, 1970 pp. 593–600.

Drokova et al., "The content of Tocopherol in Alga *Dunaliella salina*", Ukr. Bot. Zh, vol. 31(2) pp. 229–231, 1974.

Johnson et al., Journal of Bacteriology, 95(4), 1461–1468 (1968).

Yamamoto, Yoshikazu, et al., Chemical Abstracts, vol. 110, No. 9, Abstract No. 73888v, p. 507 (Feb. 27, 1989), JP 62,186,789.

Agency of Industrial Sciences and Technology, Chemical Abstracts, vol. 99, No. 21, Abstract No. 174542, p. 516 (Nov. 21, 1993), JP 58 99,475.

*Primary Examiner*—David M. Naff
*Assistant Examiner*—Michael Meller
*Attorney, Agent, or Firm*—George M. Gould; George W. Johnston; John P. Parise

[57] ABSTRACT

A tocopherol cyclase is produced in homogenous form which acts on phytyl benzoquinol derivatives to produce R', R', R'-tocopherols enantioselectively. The cyclase has a molecular weight of from about 48 kD to about 50 kD as determined by SDS-PAGE. The cyclase is isolated from *Chlorella protothecoides, Dunaliella salina* and wheat leaves of the Fidel variety.

30 Claims, 6 Drawing Sheets

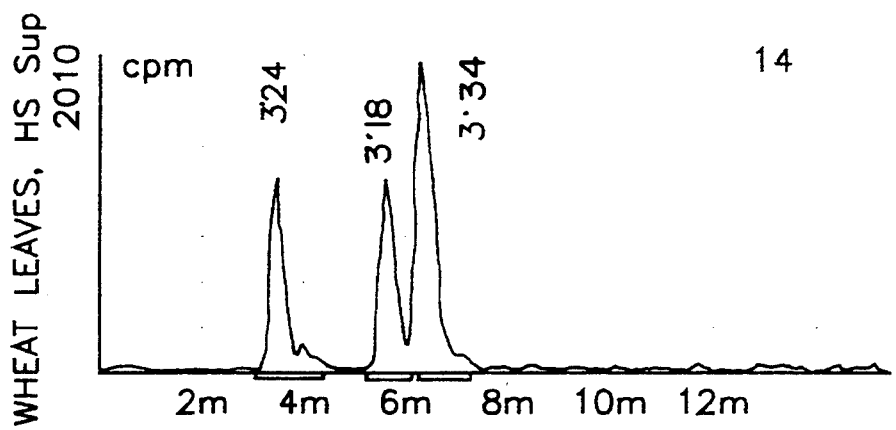

FIG. 1A

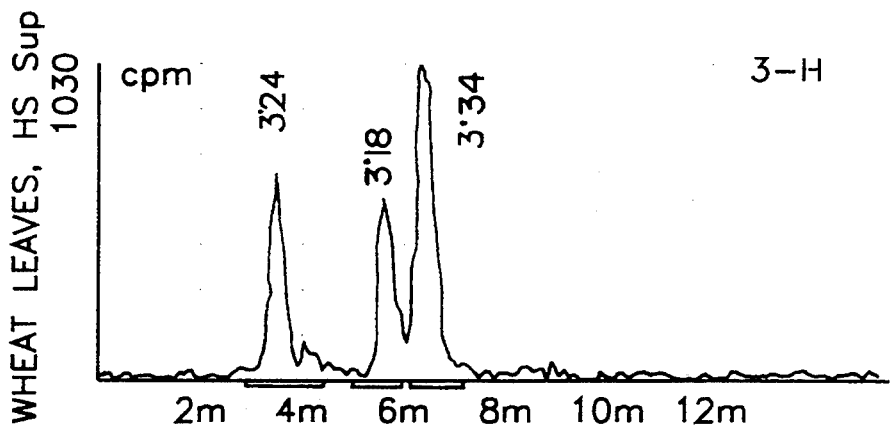

FIG. 1B

HPLC CHROMATOGRAM SHOWING THE SYNTHESIS OF (14C,3H)-GAMMA-TOCOPHEROL BY AN EXTRACT OF WHEAT LEAVES. 1ml OF WHEAT LEAF EXTRACT AS PREPARED IN EXAMPLE 1 IS INCUBATED WITH THE SUBSTRATE (14C,3H)-2,3-DIMETHYL-6-PHYTYLHYDROQUINONE. THE EXISTENCE OF TOCOPHEROL CYCLASE ACTIVITY IS INDICATED BY PRESENCE OF (14C,3H)-GAMMA-TOCOPHEROL IN THE REACTION MIX. THE HPLC CHROMATOGRAM (SEE EXAMPLE 1 FOR RUNNING CONDITIONS) SHOWS TWO SUBSTRATE PEAKS (3.2 AND 5.5 MIN) AND A GAMMA-TOCOPHEROL PEAK (5.2 MIN)

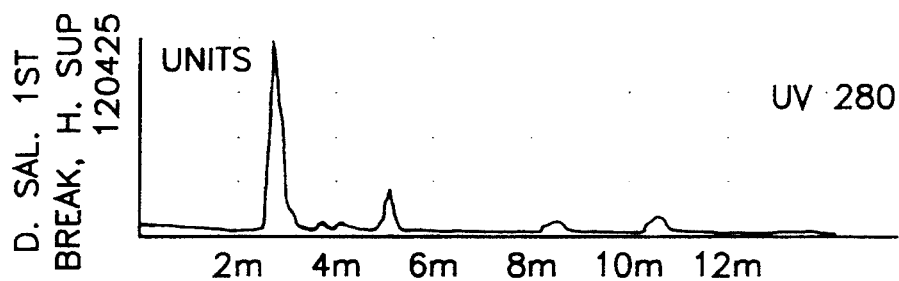

FIG. 2A

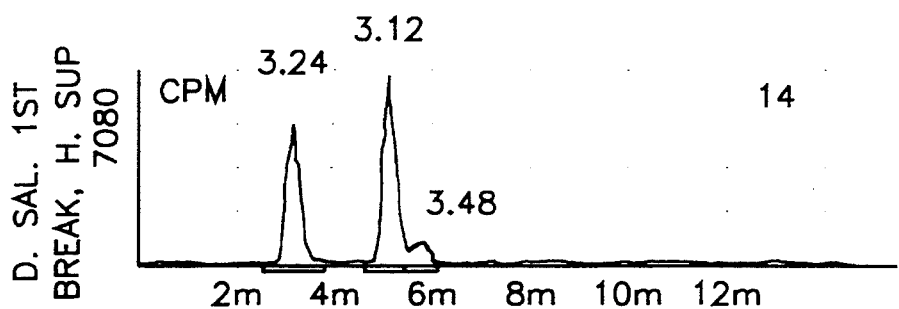

FIG. 2B

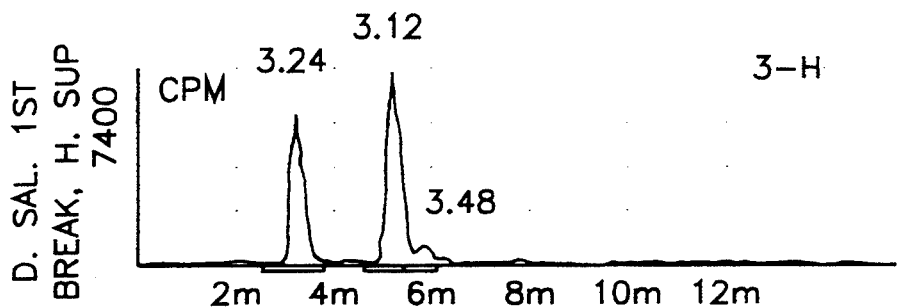

FIG. 2C

HPLC CHROMATOGRAM SHOWING THE SYNTHESIS OF ($^{14}$C,$^3$H)-GAMMA-TOCOPHEROL BY A CELL EXTRACT FROM DUNALIELLA SALINA. 1 ml OF CELL EXTRACT AS PREPARED IN EXAMPLE 2 IS INCUBATED WITH SUBSTRATE ($^{14}$C,$^3$H)-2,3-DIMETHYL-6-PHYTYLHYDROQUINONE. THE EXISTENCE OF TOCOPHEROL CYCLASE ACTIVITY IS INDICATED BY THE PRESENCE OF ($^{14}$C,$^3$H)-GAMMA-TOCOPHEROL IN THE REACTION MIX. THE HPLC CHROMATOGRAM (SEE EXAMPLE 2 FOR RUNNING CONDITIONS) SHOWS TWO SUBSTRATE PEAKS (3.2 AND 5.5 MIN) AND A GAMMA-TOCOPHEROL PEAK (5.1 MIN)

GROWTH VERSUS TOPOPHEROL CYCLASE ACTIVITY
(□———□, CELL COUNT; ●———● TOCOPHEROL CYCLASE ACTIVITY)

SDS-PAGE ANALYSIS OF ELUTION FRACTIONS FROM A PRO RPC COLUMN. FRACTIONS ELUTED FROM A PRO RPC COLUMN WITH A GRADIENT OF ISOPROPANOL (-----) ARE ASSAYED FOR TOCOPHEROL CYCLASE ACTIVITY(O———O)(ABOVE) AND ANALYSED BY SDS-PAGE(BELOW). ACTIVITY CORRELATES WITH TWO PROTEINS, WITH MOLECULAR WEIGHTS 48 AND 50kD.

| AMINO ACID | 48 | 48+50 |
|---|---|---|
| | RESIDUES/ MOLE | RESIDUES/ MOLE |
| Asx | 42,1 | 39,4 |
| Glx | 46,3 | 45,9 |
| Ser | 20,0 | 23,3 |
| His | 6,9 | 8,2 |
| Gly | 81,2 | 93,0 |
| Thr | 29,4 | 31,4 |
| Ala | 40,7 | 43,5 |
| Arg | 22,6 | 23,8 |
| Tyr | 7,4 | 7,5 |
| Cys-Cys | 16,2 | 15,5 |
| Val | 29,0 | 29,1 |
| Met | 1,7 | 2,8 |
| Ile | 9,6 | 9,3 |
| Phe | 13,9 | 14,5 |
| Leu | 42,7 | 43,4 |
| Lys | 10,0 | 16,6 |
| Pro | 37,2 | 33,3 |

AMINO ACID ANALYSES OF 48 kD TOCOPHEROL CYCLASE AND A MIXTURE OF THE 48 kD AND 50 kD TOCOPHEROL CYCLASES.

FIG. 5

TOCOPHEROL CYCLASE ISOLATED FROM *CHLORELLA PROTOTHECOIDES, DUNALIELLA SALINA* AND WHEAT LEAVES

FIELD OF THE INVENTION

The invention concerns a novel cyclase enzyme, and more particularly, a tocopherol cyclase in homogeneous, pure form.

SUMMARY OF THE INVENTION

The invention relates to the enzyme tocopherol cyclase as a homogeneous protein. The tocopherol cyclase enzyme acts on phytyl benzoquinol derivatives to produce R',R',R'-tocopherols enantioselectively (natural vitamin E). The invention also relates to a process for producing the tocopherol cyclase as a homogeneous protein. The production of tocopherol cyclase comprises the following isolation and purification-steps which are known per se, centrifugation, gel filtration, hydrophobic interaction chromatography, ion exchange chromatography, and reverse phase chromatography.

BRIEF DESCRIPTION OF THE FIGURES

FIG. 1 is a chromatogram having a peak corresponding to gamma-tocopherol indicating the presence of tocopherol cyclase in wheat leaf extract.

FIG. 2 is a chromatogram having a peak corresponding to gamma-tocopherol indicating the presence of tocopherol cyclase in *Dunaliella salina*.

FIG. 5 shows the amino acid analysis for a 48 kD tocopherol cyclase and a mixture of the 48 kD and 50 kD proteins.

DETAILED DESCRIPTION OF THE INVENTION

The invention is directed to the enzyme tocopherol cyclase as a homogeneous protein and to a process for producing the homogeneous protein.

In the homogeneous form, the enzyme has a molecular weight of 48 kD–50 kD, and contains at least one of the following amino acid sequence fragments:

-Ser-Leu-Tyr-Asp-Pro-His-Val-Pro-(Thr)-Met-Tyr-Asp-Pro-Ala-phe-(Arg)-(Thr)-[SEQ ID NO: 1];

-Xaa-Xaa-(Ala)-Val-Tyr-Val-Ala-Gln-Leu-(Arg)-Gly-Ile-Gly-(Lys)-[SEQ ID NO: 2]

-(Gly)-Ala-(Gly)-Leu-Ala-(Arg)-Phe-Glu-[SEQ ID NO: 3];

-Xaa-Asn-Ala-Leu-Tyr-Leu-Ile-Asp-Leu-Gln-Tyr-Thr-(Gly)-Gly-(Gly)-Xaa-Val-Lys-[SEQ ID NO: 4];

-Gln-Val-Pro-(Arg)-Glu-Ala-Asn-Asn-[SEQ ID NO: 5];

-Xaa-Leu-Ala-Pro-Val-Gln-(Ser)-Pro-[SEQ ID NO: 6];

-(Gly)-Leu-Asp-Leu-Ala-Pro-[SEQ ID NO: 7];

-Xaa-Val-Gln-Leu-(Asp)-(Ser)-Asp-Gly-Glu-(Thr)-Val-[SEQ ID NO: 8];

-Xaa-Leu-(Pro)-Val-[SEQ ID NO: 9];

wherein Xaa denotes at least one of the twenty-two amino acids, and the parentheses denotes uncertainty, however, the amino acid believed to occupy those respective positions are denoted.

The enzyme can be obtained from an organism having eukaryotic cells, in particular, of algal or plant origin. More particularly, it occurs in green algae, for example in *Dunaliella salina*, *Chlorella protothecoides*, or in wheat leaves.

A further embodiment of the present invention is the production of the novel enzyme.

The identification of the tocopherol cyclase encompasses the steps of SDS-PAGE electrophoresis, electroblotting, and amino acid sequencing, all of which are per se known methods in the art.

The homogeneous enzyme can thus be characterized by its above amino acid sequence.

Growth of cells, cell breakage

The photosynthetic organisms are grown in the absence of light (heterotrophic growth) or in the presence of light (autotrophic growth). In the case of heterotrophic growth, an organic carbon source is required.

The cells are cultured in an aqueous medium supplemented with appropriate nutrients under aerobic conditions. The cultivation are conducted at pH of about 4.0 to about 8.0, preferably from about 4.5 to about 6.5. The cultivation period varies depending upon the microorganisms and nutrient medium to be used, preferably about 10 to about 100 hours. A preferred temperature range for carrying out for the cultivation is from about 10° C. to about 40° C., preferably from about 25° C. to about 35° C. The addition to and amount of such constituents are within the skill of an ordinary artisan.

It is usually required that the culture medium contains nutrients such as: assimilable carbon sources (heterotrophic only) such as D-glucose, sodium acetate, etc.; digestible nitrogen sources such as organic substances, for example, peptone, yeast extract, etc.; and inorganic substances, for example, ammonium sulfate, ammonium chloride and potassium nitrite; vitamins and trace elements.

Figure 3:
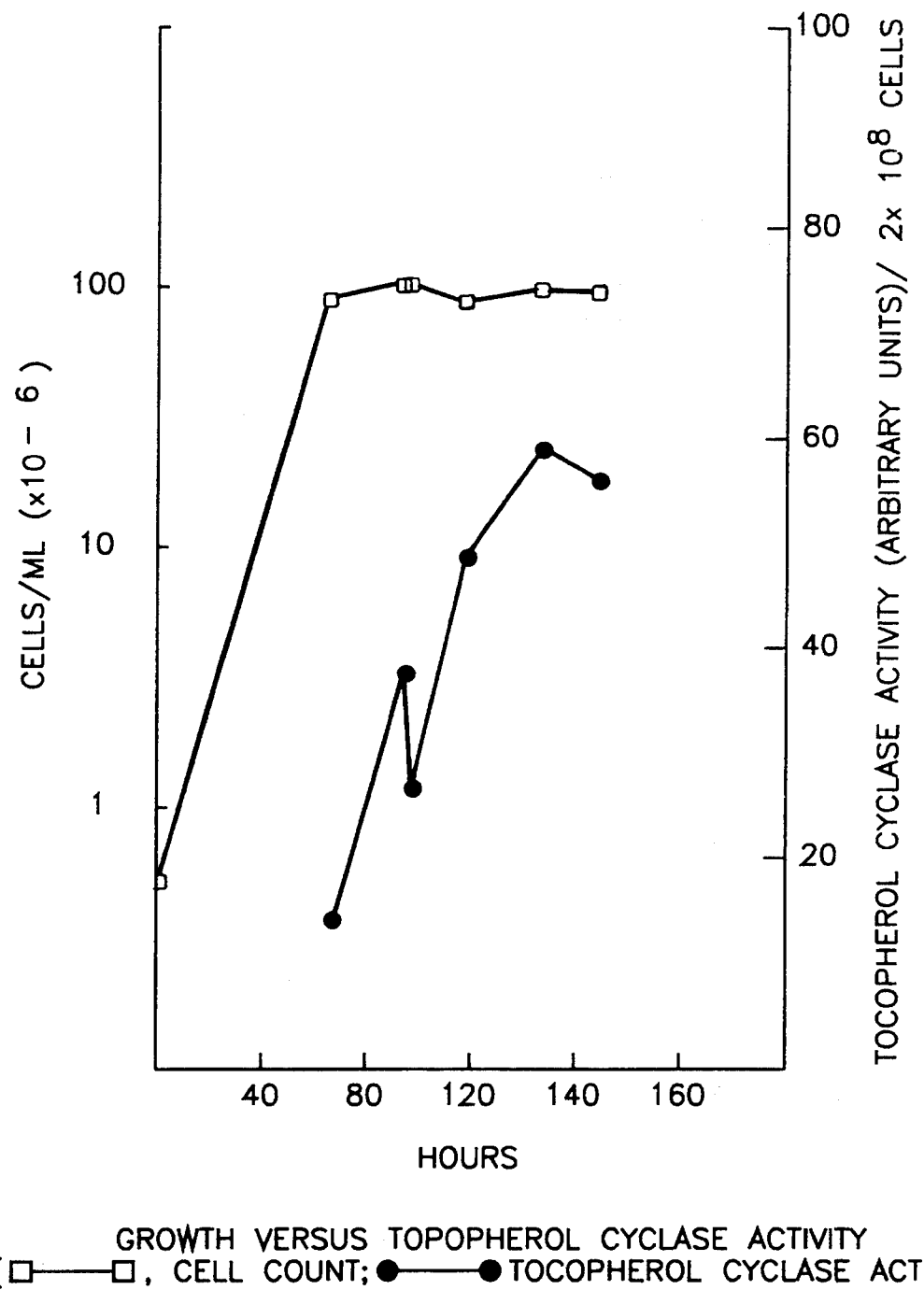
FIG. 3 shows tocopherol cyclase activity versus cell growth.

The enzyme activity is absent in logarithmically growing cells and starts to appear only at the beginning of stationary phase where it rapidly rises to a maximum value, then levels off (FIG. 3). Cells can thus be harvested at maximal cell density. The cell yield is typically around 20 g/l (wet weight) under heterotrophic conditions. Markedly higher levels of enzyme activity are observed when the cells are grown autotrophically. However much lower cell densities ensue when cells are grown autotrophically.

During fermentation, tocopherol cyclase activity is measured by harvesting a fixed number of cells, e.g. about $1 \times 10^9$, and lysing them mechanically; the supernatant obtained by centrifuging the lysate at $100000 \times g$ for 30 min is mixed with radiolabelled 2,3-dimethyl-6-phytylhydroquinone and the mixture incubated for 12–15 hr at 30° C. under reducing conditions. Radiolabelled hydroquinone and gamma-tocopherol are extracted into hexane, separated by HPLC and quantitated by radiodetection.

A convenient scheme for the isolation and purification of the enzyme after the cultivation of cells is as follows:

1) cells are harvested from the fermentation broth by centrifugation;

2) the cells are suspended in the buffer solution and disrupted mechanically, i.e. lysed by means of a homogenizer, to give a disrupted suspension. A convenient buffer is of the phosphate type;

3) the soluble enzyme is isolated and purified from the soluble extract of the disrupted cells following removal of cell membranes by centrifugation, as described below.

Centrifugation

Cells containing tocopherol cyclase activity are conveniently harvested, e.g. by continuous centrifugation and stored at $-20°$ C. until required. Enzyme activity remains stable over several months. Cells to be used are thawed into an excess, e.g. an 2.5 fold excess, of potassium phosphate buffer, pH 7. The suspension is lysed mechanically, e.g. by rotation with glass beads and the resulting lysate centrifuged to remove cell debris. The supernatant obtained by centrifugation is made ca. 60% saturated with ammonium sulphate in order to precipitate the proteins. The resulting precipitate is removed by centrifugation and resuspended in a small volume of the potassium phosphate buffer.

Gel filtration (molecular sizing chromatography)

With this technique proteins are separated according to molecular weight. The preferred matrix is one which allows separation of proteins in the molecular weight range 5000-250000 D, e.g. Sephacryl S-200HR. In this instance the gel filtration step serves to separate the tocopherol cyclase (activity) from the bulk of colored components in the cell extract. In the present sequence of steps, it serves thus as a preliminary purification step.

The material to be chromatographed is loaded onto the column in aqueous buffer at pH 6.5-7. A convenient buffer is of the phosphate type. After chromatography, those fractions containing tocopherol cyclase activity are selected for further purification.

Since the activity is contained in a large volume, concentration of the material is necessary before the next purification step. The active fractions can be conveniently concentrated on a (small) bed of a strong anion exchanger, such as Q-Sepharose. The material is loaded in dilute salt solution whereupon it binds tightly to the anion exchanger; it can then be eluted with a small volume of concentrated salt solution. Ca. 0.4-0.8M alkali halide is appropriate.

Hydrophobic interaction chromatoagraphy

As is known, this technique is based on the interaction between the aliphatic chains on the adsorbent and the corresponding hydrophobic regions on the surface of the proteins, causing proteins to bind. The adsorbents preferably used are the commercially available $C_4$ linear aliphatic chain materials, e.g. Butyl-Sepharose, since the cyclase to be purified is considered to be medium to weakly hydrophobic.

The material to be separated is adsorbed onto the column in high salt solution and is eluted with a reverse and linear salt gradient.

The preferred salt is ammonium sulfate. The initial salt concentration is ca. 600-700 mM and the final salt concentration is ca. 0-20 mM.

After this purification step, the product is conveniently dialyzed in order to remove the ammonium sulphate.

Ion-exchange chromatography

In the present case anion-exchange is the method of choice: thus the negatively charged regions of proteins are exploited for adsorption to a positively charged matrix.

A strong anion exchanger containing quarternary amines as charged groups is the preferred exchanger (e.g. Mono Q). Proteins are adsorbed in a buffer containing little salt, at pH 7, and eluted with a gradient of buffer containing high salt concentrations, e.g. ca. 1M of an alkali halide, e.g. 1M KCl.

The initial salt concentration is ca. 0-20 min. The final salt concentration is ca. 300-500 mM.

The gradient is preferably linear.

Reverse phase chromatography

This term is used in the present context to refer to the methods known in the art, with the difference that organic solvents and a somewhat more hydrophobic adsorbent are used. The proteins are absorbed onto a column in a buffer solution and eluted with an increasing gradient of the organic solvent. A convenient buffer is of the phosphate type. A convenient column material is Pro RPC, a macro-porous microparticulate silica with bonded $C_1/C_8$ groups.

Convenient parameters are:
initial solvent: ca. 0-10% isopropanol
final solvent: ca. 30-50% isopropanol This purification steps allows the separation of two cyclases of molecular weights of 48 and 50 kD from remaining impurities.

SDS-PAGE and Electroblotting

As is known, the mobility of proteins in polyacrylamide gels in the presence of SDS is a linear function of the logarithm of their molecular weight.

The method thus allows the purity of a protein to be analyzed or it can also be used as a purification method per se.

In the present case SDS-PAGE is used essentially as an analytical step but, followed by electroblotting, it is also a convenient method to prepare the tocopherol cyclase as an enzymatically active homogeneous protein in a suitable form for N-terminal sequence analysis.

After electrophoresis, the gel is conveniently electroblotted to a PVDF (polyvinylidene fluoride) membrane and the transferred proteins further characterized.

The enzymes thus purified can now be characterized by state-of-the-art peptide chemistry methods, such as N-terminal amino acid sequencing with enzymatic or chemical peptide cleavage. Fragments obtained by enzymatic or chemical cleavage can be separated according to usual methods, such as HPLC, and can themselves be subjected to further N-terminal sequencing. The experimental details are outlined in the Examples.

Assay for the novel cyclase

The assay for the novel cyclase described for fermentation analysis above in Examples 1 and 2 below was also used to monitor the cyclase activity following:
gel filtration
hydrophobic interaction chromatography
ion exchange chromatography
reverse phase chromatography.

It makes use of the ability of the novel cyclase to catalyze the reaction of 2,3-dimethyl-6-phytylhydroquinone to R',R',R',γ-tocopherol.

Unless indicated to the contrary, the following non-limiting examples were carried out as written.

EXAMPLE 1

Identification of tocopherol cyclase activity in wheat leaves.

40 g of wheat grains (variety Fidel) are washed in 70% (vol.) ethanol for 5 minutes, then rinsed in $H_2O$; the grains are then aereated for 2–4 hrs in $H_2O$. They are subsequently distributed evenly on wet filter paper in a 30×50 cm seed tray and incubated at 30° C. in the dark for 3 days. The germinated grains are then brought into the light and allowed to grow for ca. 2 weeks at ambient light and temperature.

The leaves from one tray of plants are rapidly frozen by immersion in liquid $N_2$ and immediately ground into a fine powder with pestle and mortar. The powder is then mixed with 250 ml of a buffer comprising 30 mM potassium phosphate pH 7, 1 mM dithiothreitol, 10% sucrose, 5 mM sodium ascorbate and stirred at 4° C. for 1 hr.

The suspension is centrifuged at 2000×g for 10 minutes, then at 40000×g for 1 hr. This high speed supernatant is then assayed for tocopherol cyclase activity by adding the substrate ($^3H$,$^{14}C$-)2,3-dimethyl-6-phytyl-hydroquinone and incubating at 30° C. for 15 hr. The incubation mixture is extracted with hexane:methanol (1:4) and the hexane phase injected onto a 220×4.6 mm Spheri-5 silica HPLC column (Kontron Analytics); the column is eluted isocratically with hexane:isopropanol (99:1). Under these conditions the dimethylphytylbenzoquinone is not retained by the column and elutes at ca. 3 min; the hydroquinone form of the substrate elutes at ca. 6 min and gamma-tocopherol at ca. 5 min. The chromatogram shown in FIG. 1 contains a peak corresponding to gamma-tocopherol, indicating the presence of an enzyme with tocopherol cyclase activity in this wheat leaf extract.

EXAMPLE 2

Identification of tocopherol cyclase activity in *Dunaliella salina*.

A *Dunaliella salina* inoculum was obtained from Western Biotechnology Ltd, Australia. Cells are cultured in 2 l Erlenmeyer flasks containing 1 l of medium at ambient temperature and light. The culture medium is modified Johnson's medium (Johnson et al., J. Bacteriology 95 (1968) pp 1461–1468) containing 4.3M NaCl. Cultures are assessed to be in stationary phase when they become visibly orange (senescent cultures produce carotenoids in the presence of high salt concentrations), which corresponds to a cell count of ca. $5 \times 10^5$ cells/ml.

Cells are pelleted by centrifugation and resuspended at a concentration of ca. $2 \times 10^8$/ml in 30 mM potassium phosphate buffer pH 7, containing 10% sucrose, 4 mM $MgSO_4$, 0.2 mM EDTA. The suspension is then sonicated briefly, centrifuged at 100000×g for 1 hr and the resulting supernatant diluted 10-fold in 100 mM potassium phosphate pH 7 for assay. The assay is performed as in Example 1. The chromatogram of FIG. 2 shows the presence of a peak at ca. 5 min which corresponds to gamma-tocopherol. *Dunaliella salina* would therefore appear to contain a tocopherol cyclase.

EXAMPLE 3

Growth of *Chlorella protothecoides* and identification of tocopherol cyclase activity.

*Chlorella protothecoides* Krüger 1894 (CCAP 211/8D) was obtained from the Culture Collection of Algae and Protozoa in Cumbria, England. Cells are grown in 10 l blade-stirred glass fermentors under essentially heterotrophic growth conditions (fermentors are exposed to dim laboratory light during the day). The fermentation medium is as follows:

| yeast extract (BBL) | 100 g |
| --- | --- |
| peptone | 100 g |
| glucose | 200 g | made up to 10 L with distilled $H_2O$.

Fermentation is carried out at 30° C. and at a stir rate of 160 rpm. A sample of cells is withdrawn daily for tocopherol cyclase activity assay. After completion of fermentation the cells are centrifuged and stored as pellets at −20° C. until required for purification.

The assay is prepared by centrifuging down and resuspending $1 \times 10^9$ cells in 5 ml of 30 mM potassium phosphate pH 7, 10% (wt/vol) glycerol, 0.01% (wt/vol) lauryl maltoside. The suspension is mixed with 7 g of 0.5 mm glass beads, frozen, then shaken for 3 min in a Braun Homogeniser. The lysate is subsequently centrifuged at 100000×g for 40 min and 1 ml of the resulting supernatant taken for assay. The assay is performed as in Example 1. Relative activity of the enzyme is expressed as the percentage of total radioactivity incorporated into gamma-tocopherol by $2 \times 10^8$ cells. FIG. 3 shows growth versus activity for *C. protothecoides*. Tocopherol cyclase activity is only measurable once the cells start to enter stationary phase and cells are thus harvested after 5 days in stationary phase. The cell yield is ca. 20 g/l (wet weight).

EXAMPLE 4

Purification of Tocopherol cyclase from *C. protothecoides*.

a. Cell lysis and Dreparation of a crude extract.

300 g of cells (see Example 3) are thawed and suspended in 750 ml of 30 mM potassium phosphate pH 7, 10% (wt/vol) glycerol, 1 mM phenylmethylsulphonyl fluoride (PMSF; a protease inhibitor), 5 mM sodium ascorbate. The cells are then broken mechanically by rotation with glass beads, for example with a Dyno-Mill cell disintegrator (W. Bachofen Maschinenfabrik AG, Basel). The suspension is pumped continuously at a rate of ca. 30 ml/min through the Dyno-Mill operating at 2000 rpm. The cell suspension and the resulting lysate are kept on ice. The lysate is subsequently centrifuged at 10000×g for 15 min to remove unbroken cells and cell debris. The supernatant from this centrifugation step is then centrifuged at 100000×g for 1 hr. The second supernatant is then made 60% saturated with ammonium sulphate and stirred for 30 min at ambient temperature. The precipitate is removed by centrifugation and resuspended in 250 ml of 20 mM potassium phosphate pH 7, 10% glycerol. This material is then divided into 50 ml portions and stored at −20° C. until required.

b. Gel filtration on SephaCryl S-200HR.

A 50 ml portion of crude extract is thawed and loaded onto a molecular sizing column, for example a 5×70 cm Sephacryl S-200HR column (Pharmacia LKB), equilibrated in 20 mM potassium phosphate pH 7, 10% glycerol and pumped at a rate of 200 ml/hr. Fractions of 10 ml are collected and assayed for tocopherol cyclase activity. Active fractions are pooled and stored at −20° C. until required.

c. Concentration on Q-Sepharose.

The active pool from above is thawed and diluted 1:1 with 10% glycerol. This protein solution can then be concentrated on a small bed of the strong anion exchange resin, Q-Sepharose (Pharmacia LKB). Thus the material is passed over a 2.5×1 cm bed of Q-Sepharose equilibrated in 10 mM potassium phosphate pH 7, 10% glycerol. The column is then washed with the same buffer and eluted with 15 ml of 15 mM potassium phosphate pH 7, 10% glycerol, 400 mM NaCl.

d. Chromatography on Butyl-Sepharose.

The eluate from above is made 15% saturated with ammonium sulphate. This material is then further purified by hydrophobic interaction chromatography on a $C_4$ matrix, i.e. Butyl-Sepharose (Pharmacia LKB). It is loaded onto a 1.6×12.5 cm Butyl-Sepharose column equilibrated in 15 mM potassium phosphate pH 7, 15% (saturation) ammonium sulphate, 10% glycerol. The column is washed with the same buffer and eluted with a 0–100% gradient of 10% glycerol, 30% ethylene glycol (total gradient volume=100 ml). Fractions of 5 ml are collected and assayed for tocopherol cyclase activity. Active fractions are pooled.

e. Chromatography on Mono Q.

The active pool from above is made 0.025% (wt/vol) in lauryl maltoside and dialysed for 15 hr at 4° C. against 15 mM potassium phosphate pH 7, 10% glycerol in order to remove ammonium sulphate. This material is then loaded on a column of the compact anion exchange resin Mono Q in a HR5/5 column (Pharmacia LKB) which has been equilibrated in 15 ram potassium phosphate pH 7, 10% glycerol, 0.025% lauryl maltoside. The column is washed with this buffer and eluted at a flow rate of 1 ml/min with a gradient of 15 mM potassium phosphate pH 7, 10% glycerol, 0.025% lauryl maltoside, 1M KCl (Buffer B); the (linear) gradient has the following profile:

| 0–30% Buffer B  | 15 ml |
| 30% Buffer B    | 2 ml  |
| 30–50% Buffer B | 3 ml  |
| 50% Buffer B    | 2 ml  |

1 ml fractions are collected and assayed for tocopherol cyclase activity. The active fractions are pooled.

f. Chromatography on ProRPC.

Figure 4A:
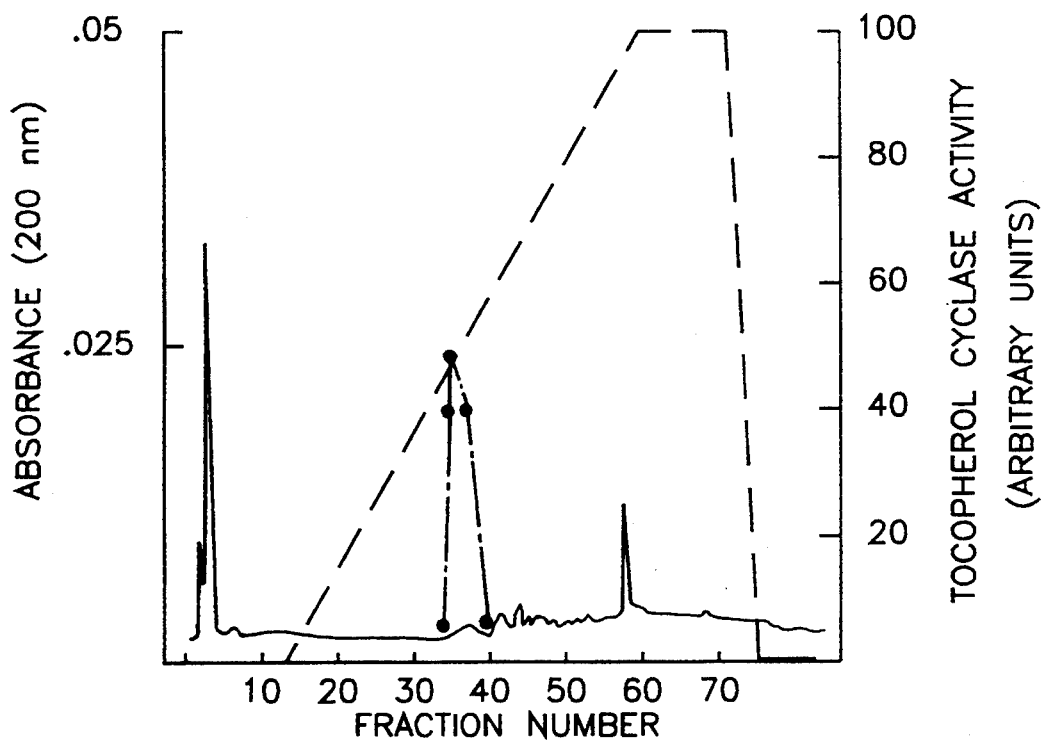
FIG. 4 shows the chromatogram and the corresponding SDS-PAGE gel of tocopherol cyclase from *Chlorella protothecoides*.
Figure 4B:
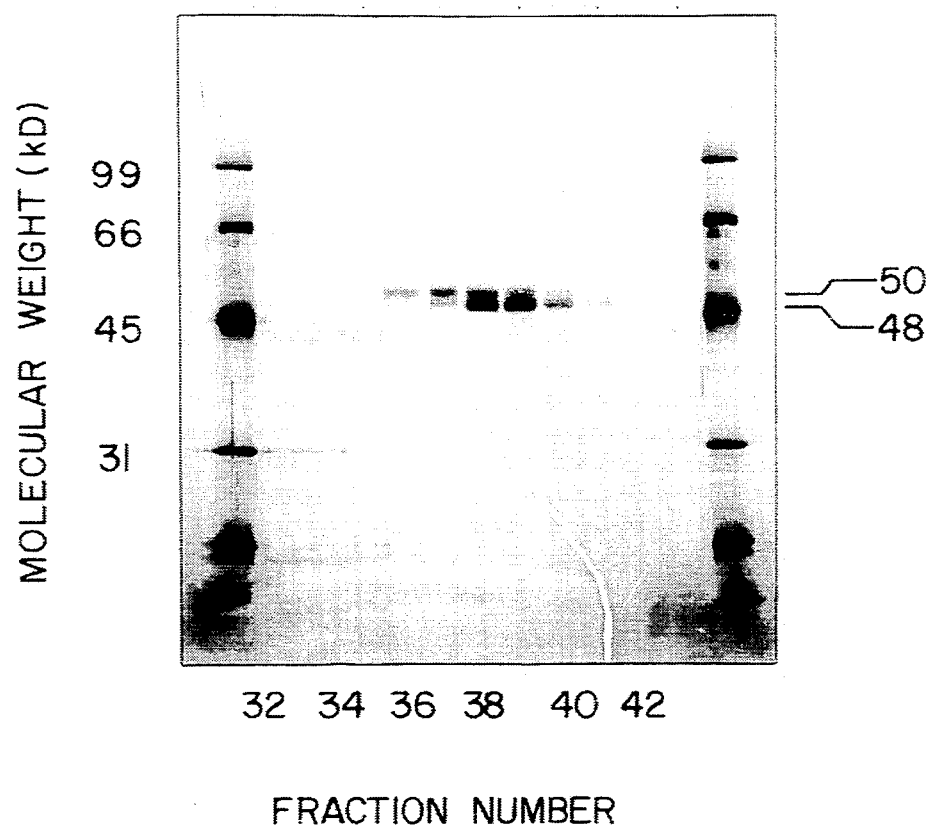

A C1/C8 reverse phase column, i.e. a ProRPC HR5/10 column from Pharmacia LKB is used for further purification. The ProRPC column is equilibrated in 5 mM potassium phosphate buffer pH 7.1 ml of the active pool from above is loaded onto the column. The column is then washed with 10% isopropanol and eluted at 0.5 ml/min with a linear gradient to 50% isopropanol (total gradient volume=25 ml). Fractions of 0.5 ml are collected and every second assayed for tocopherol cyclase activity. Samples are also withdrawn from every fraction for SDS-PAGE analysis. FIG. 4 shows the chromatogram and the results of the activity measurements; this figure also shows the corresponding SDS-PAGE gel. The cyclase activity is associated with 2 proteins, one of molecular weight ca. 50 kD and the other with a molecular weight of 48 kD.

EXAMPLE 5

Separation of 48 kD and 50 kD Tocopherol Cyclases for Amino Acid Analysis and Protein Sequence Analysis.

Following chromatography on ProRPC, fractions containing tocopherol cyclase activity are pooled (total volume=6.5 ml) and concentrated to ca. 350 μl. Of this, 30 μl are removed and the quality and quantity assessed by SDS-PAGE with Coomassie Blue staining. The remaining 320 μl are mixed with 35 μl denaturing buffer containing the reducing agent mercaptoethanol (U.K. Laemmli [1970] Nature 227,680–685) and heated at 95° C. until the volume reduces to 140 μl. The protein is then electrophoresed on an 8% SDS-PAGE gel. After electrophoresis the gel is used for electroblotting to a polyvinylidene fluoride (PVDF) membrane (Immobilon P, Millipore); blotting is carried out in 10 mM 3-(cyclohexylamino)-1-propane sulphonic acid (CAPS) buffer pH 11, 10% (vol/vol) methanol (Matsudaira, P. [1987] J. Biol. Chem. 261, 10035–10038) for 1 hr at 90 V and at 4° C. The PVDF membrane is subsequently stained with 0.5% Poneeau S in 1% acetic acid to visualize the transferred protein. A strip of membrane containing the tocopherol cyclase band is then excised and stored at −20° C. until required.

ProRPC chromatography does not result in the resolution of 48 and 50 kD tocopherol cyclases. Consequently pooled active material contains both forms. However if the protein is subsequently electrophoresed on an 8% SDS-PAGE gel in the absence of mercaptoethanol the 48 and 50 kD proteins resolve from each other (in the presence of mercaptoethanol the two proteins do not resolve). This observation can be utilized to purify the 48 kD tocopherol cyclase for amino acid and protein sequence analysis by the method described above. Thus mercaptoethanol was excluded from the dissociation buffer and, following electroblotting and Ponceau staining of the PVDF membrane, the two proteins were individually excised.

EXAMPLE 6

Amino Acid Analysis and Amino Acid Sequence Analysis of the Two Tocopherol Cyclases A. Amino Acid Analysis The membrane fragments prepared in Example 5 are incubated in the presence of 6N HCl for 24 hr at 110° C. The hydrolysed amino acids are extracted from the membranes with 2×100 μl formic acid (1 hr incubation at 37° C.) and analyzed according to standard procedures on an AminoQuant amino acid analyser (Hewlett Packard). Amino acid analyses (FIG. 5) for the 48 kD cyclase and a mixture of the 48 kD and 50 kD proteins show that the two cyclases are closely related.

B. Amino Acid Sequence Analysis

The membrane fragments prepared as in Example 5 are rinsed with water and air-dried. They are then treated with either trypsin or Proteinase K in situ and the peptides obtained separated by reverse phase HPLC.

Trypsin cleavage. The membrane piece containing the protein band is placed in an Eppendorf tube containing 1 ml of PVP-30 solution (polyvinylpyrrolidone in 100 mM acetic acid) and incubated at 37° C. for 30 min. The PVP-30 solution is then removed and the membrane thoroughly washed with 10 ml of water. It is then cut into small pieces and transferred to a clean Eppendorf tube containing 200 μl of 100 mM ammonium bicarbonate pH 8.0. A solution of 10 ng of trypsin in 0.1% trifluoroacetic acid (TFA) is added and the mixture is incubated at 37° C. for 24 hr. The cleavage is stopped by addition of 5 μl of 10% TFA. The solution is then transferred into a clean Eppendorf tube; the membrane pieces are washed with 100 μl of 10% TFA and the wash combined with the above solution.

Endoproteinase Lys-C cleavage. The procedure is the same as for trypsin except that Endoproteinase Lys-C is used.

Proteinase K cleavage. The procedure is the same as for trypsin except that buffers contain additionally 2M guanidinium hydrochloride and 50 ng of Proteinase K is used in place of trypsin. After 24 hr incubation an additional 50 ng of Proteinase K is added and the incubation continued for 3 hr.

The trypsin, Endoproteinase Lys-C and Proteinase K cleavage products are separated on a reverse phase HPLC column (Aquapore RP-300, 1×100 mm, C8, Brownlee/Applied Biosystems) according to standard procedures. The separated peptides are then analyzed on an automated pulsed liquid microsequencing apparatus (Applied Biosystems, Model 475A, Foster City, Calif., USA) with automatic on-line amino acid analysis (Applied Biosystems, Amino Acid Analyser Model 120, Foster City, Calif., USA). The following sequence information was obtained:

48 kD Tocopherol Cyclase, Proteinase K cleavage

-Xaa-Leu-Ala-Pro-Val-Gln-(Ser)-Pro-[SEQ ID NO: 6];
-(Gly)-Leu-Asp-Leu-Ala-Pro-[SEQ ID NO: 7];
-Xaa-Val-Gln-Leu-(Asp)-(Ser)-Asp-Gly-Glu-(Thr)-Val-[SEQ ID NO: 8];
-Xaa-Leu-(Pro)-Val-[SEQ ID NO: 9];

where Xaa and -()- are as defined previously.

50 kD Tocopherol cyclase, Endoproteinase Lys-C cleavage

-Xaa-Xaa-(Ala)-Val-Tyr-Val-Ala-Gln-Leu-(Arg)-Gly-Ile-Gly-(Lys)-[SEQ ID NO: 2]
(Gly)-Ala-(Gly)-Leu-Ala-(Arg)-Phe-Glu-[SEQ ID NO: 3];
-Xaa-Asn-Ala-Leu-Tyr-Leu-Ile-Asp-Leu-Gln-Tyr-Thr-(Gly)-Gly-(Gly)-Xaa-Val-Lys-[SEQ ID NO: 4];
-Gln-Val-Pro-(Arg)-Glu-Ala-Asn-Asn-[SEQ ID NO: 5];

where Xaa and -()- are as defined previously.

50 kD tocopherol cyclase, direct N-terminal sequencing

-Ser-Leu-Tyr-Asp-Pro-His-Val-Pro-(Thr)-Met-Tyr-Asp-Pro-Ala-Phe-(Arg)-(Thr)-[SEQ ID NO. 1]

where Xaa and -()- are as defined previously.

---

What is claimed is:

1. A tocopherol cyclase isolated from *Chlorella protothecoides, Dunaliella salina* or wheat leaves of the Fidel variety, and having the following properties:
   a) a molecular weight of from about 48 kD to about 50 kD, as determined by SDS-PAGE;
   b) at least one amino acid sequence fragment selected from the group consisting of:
      -Ser-Leu-Tyr-Asp-Pro-His-Val-Pro-Xaa-Met-Tyr-Asp-Pro-Ala-Phe-Xaa-Xaa-(SEQ ID NO: 1);
      -Xaa-Xaa-Xaa-Val-Tyr-Val-Ala-Gln-Leu-Xaa-Gly-Ile-Gly-Xaa-(SEQ ID NO: 2);
      -Xaa-Ala-Xaa-Leu-Ala-Xaa-Phe-Glu-(SEQ ID NO: 3);
      -Xaa-Asn-Ala-Leu-Tyr-Leu-Ile-Asp-Leu-Gln-Tyr-Thr-Xaa-Gly-Xaa-Xaa-Val-Lys-(SEQ ID NO: 4);
      -Gln-Val-Pro-Xaa-Glu-Ala-Asn-Asn-(SEQ ID NO: 5);
      -Xaa-Leu-Ala-Pro-Val-Gln-Xaa-Pro-(SEQ ID NO: 6);
      -Xaa-Leu-Asp-Leu-Ala-Pro-[SEQ ID NO: 7);
      -Xaa-Val-Gln-Leu-Xaa-Xaa-Asp-Gly-Glu-Xaa-Val-(SEQ ID NO: 8); and
      -Xaa-Leu-Xaa-Val-(SEQ ID NO: 9), and
   c) acts on phytyl benzoquinol derivatives to produce R', R',R'-tocopherols enantioselectively.

2. The tocopherol cyclase according to claim 1 wherein the tocopherol cyclase enantioselectively produces R',R',R'-γ-tocopherol.

3. The tocopherol cyclase according to claim 1 isolated from a soluble fractions of *Chlorella protothecoides* or *Dunaliella salina*.

4. A tocopherol cyclase isolated from a *Chlorella protothecoides, Dunaliella salina* or wheat leaves of the Fidel variety, and having the following properties:
   a) a molecular weight of from about 48 kD to about 50 kD, as determined by SDS-PAGE;
   b) at least one amino acid sequence fragment selected from the group consisting of:
      -Ser-Leu-Tyr-Asp-Pro-His-Val-Pro-Thr-Met-Tyr-Asp-Pro-Ala-Phe-Arg-Thr-(SEQ ID NO: 10);
      -Xaa-Xaa-Ala-Val-Tyr-Val-Ala-Gln-Leu-Arg-Gly-Ile-Gly-Lys-(SEQ ID NO: 11);
      -Gly-Ala-Gly-Leu-Ala-Arg-Phe-Glu-(SEQ ID NO: 12);
      -Xaa-Asn-Ala-Leu-Tyr-Leu-Ile-Asp-Leu-Gln-Tyr-Thr-Gly-Gly-Gly-Xaa-Val-Lys-(SEQ ID NO: 13);
      -Gln-Val-Pro-Arg-Glu-Ala-Asn-Asn-(SEQ ID NO: 14);
      -Xaa-Leu-Ala-Pro-Val-Gln-Ser-Pro-(SEQ ID NO: 15);
      -Gly-Leu-Asp-Leu-Ala-Pro-(SEQ ID NO: 16);
      -Xaa-Val-Gln-Leu-Asp-Ser-Asp-Gly-Glu-Thr-Val-(SEQ ID NO: 17); and
      -Xaa-Leu-Pro-Val-(SEQ ID NO: 18)
   c) acts on phytyl benzoquinol derivatives to produce R',R',R'-tocopherols enantioselectively.

5. The tocopherol cyclase according to claim 4, wherein the amino acid sequence fragment is -Ser-Leu-Tyr-Asp-Pro-His-Val-Pro-Thr-Met-Tyr-Asp-Pro-Ala-Phe-Arg-Thr-(SEQ ID NO: 10).

6. The tocopherol cyclase according to claim 4, wherein the amino acid sequence fragment is -Xaa-Xaa-Ala-Val-Tyr-Val-Ala-Gln-Leu-Arg-Gly-Ile-Gly-Lys-(SEQ ID NO: 11).

7. The tocopherol cyclase according to claim 4, wherein the amino acid sequence fragment is -Gly-Ala-Gly-Leu-Ala-Arg-Phe-Glu-(SEQ ID NO: 12).

8. The tocopherol cyclase according to claim 4, wherein the amino acid sequence fragment is -Xaa-Asn-Ala-Leu-Tyr-Leu-Ile-Asp-Leu-Gln-Tyr-Thr-Gly-Gly-Gly-Xaa-Val-Lys-(SEQ ID NO: 13).

9. The tocopherol cyclase according to claim 4, wherein the amino acid sequence fragment is -Gln-Val-Pro-Arg-Glu-Ala-Asn-Asn-(SEQ ID NO: 14).

10. The tocopherol cyclase according to claim 4, wherein the amino acid sequence fragment is -Xaa-Leu-Ala-Pro-Val-Gln-Ser-pro-(SEQ ID NO: 15).

11. The tocopherol cyclase according to claim 4, wherein the amino acid sequence fragment is -Gly-Leu-Asp-Leu-Ala-Pro-(SEQ ID NO: 16).

12. The tocopherol cyclase according to claim 4, wherein the amino acid sequence fragment is -Xaa-Val-Gln-Leu-Asp-Ser-Asp-Gly-Glu-Thr-Val-(SEQ ID NO: 17).

13. The tocopherol cyclase according to claim 4, wherein the amino acid sequence fragment is -Xaa-Leu-Pro-Val-(SEQ ID NO: 18).

14. The tocopherol cyclase according to claim 4 wherein the tocopherol cyclase enantioselectively produces R',R',R'-γ-tocopherol.

15. The tocopherol cyclase according to claim 4 isolated from a soluble extract of *Chlorella protothecoides* or *Dunaliella salina*.

16. A tocopherol cyclase purified to homogeneity from *Chlorella protothecoides, Dunaliella salina* or wheat leaves of the Fidel variety, and having the following properties:
   a) a molecular weight of from about 48 kD to about 50 kD as determined by SDS-PAGE;
   b) at least one amino acid sequence fragment selected from the group consisting of:
      -Ser-Leu-Tyr-Asp-Pro-His-Val-Pro-Xaa-Met-Tyr-Asp-Pro-Ala-Phe-Xaa-Xaa-(SEQ ID NO: 1);
      -Xaa-Xaa-Xaa-Val-Tyr-Val-Ala-Gln-Leu-Xaa-Gly-Ile-Gly-Xaa-(SEQ ID NO: 2);
      -Xaa-Ala-Xaa-Leu-Ala-Xaa-Phe-Glu-(SEQ ID NO: 3);
      -Xaa-Asn-Ala-Leu-Tyr-Leu-Ile-Asp-Leu-Gln-Tyr-Thr-Xaa-Gly-Xaa-Xaa-Val-Lys-(SEQ ID NO: 4);
      -Gln-Val-Pro-Xaa-Glu-Ala-Asn-Asn-(SEQ ID NO: 5);
      -Xaa-Leu-Ala-Pro-Val-Gln-Xaa-Pro-(SEQ ID NO: 6);
      -Xaa-Leu-Asp-Leu-Ala-Pro-(SEQ ID NO: 7);
      -Xaa-Val-Gln-Leu-Xaa-Xaa-Asp-Gly-Glu-Xaa-Val-(SEQ ID NO: 8); and
      -Xaa-Leu-Xaa-Val-(SEQ ID NO: 9), and
   c) acts on phytyl benzoquinol derivatives to produce R',R',R'-tocopherols enantioselectively.

17. The tocopherol cyclase according to claim 16 wherein the tocopherol cyclase enantioselectively produces R',R',R'-γ-tocopherol.

18. The tocopherol cyclase according to claim 16 isolated from a soluble extract of *Chlorella protothecoides* or *Dunaliella salina*.

19. A tocopherol cyclase purified to homogeneity from *Chlorella protothecoides, Dunaliella salina* or wheat leaves of the Fidel variety, and having the following properties:
   a) a molecular weight of from about 48 kD to about 50 kD as determined by SDS-PAGE;
   b) at least one amino acid sequence fragment selected from the group consisting of:
      -Ser-Leu-Tyr-Asp-Pro-His-Val-Pro-Thr-Met-Tyr-Asp-Pro-Ala-Phe-Arg-Thr-(SEQ ID NO: 10);
      -Xaa-Xaa-Ala-Val-Tyr-Val-Ala-Gln-Leu-Arg-Gly-Ile-Gly-Lys-[SEQ ID NO: 11);
      -Gly-Ala-Gly-Leu-Ala-Arg-Phe-Glu-(SEQ ID NO: 12);
      -Xaa-Asn-Ala-Leu-Tyr-Leu-Ile-Asp-Leu-Gln-Tyr-Thr-Gly-Gly-Gly-Xaa-Val-Lys-(SEQ ID NO: 13);
      -Gln-Val-Pro-Arg-Glu-Ala-Asn-Asn-(SEQ ID NO: 14);
      -Xaa-Leu-Ala-Pro-Val-Gln-Ser-Pro-(SEQ ID NO: 15);
      -Gly-Leu-Asp-Leu-Ala-Pro-(SEQ ID NO: 16);
      -Xaa-Val-Gln-Leu-Asp-Ser-Asp-Gly-Glu-Thr-Val-(SEQ ID NO: 17); and
      -Xaa-Leu-Pro-Val-(SEQ ID NO: 18), and
   c) acts on phytyl benzoquinol derivatives to produce R',R',R'-tocopherols enantioselectively.

20. The tocopherol cyclase according to claim 19, wherein the amino acid sequence fragment is -Ser-Leu-Tyr-Asp-Pro-His-Val-Pro-Thr-Met-Tyr-Asp-Pro-Ala-Phe-Arg-Thr-(SEQ ID NO: 10).

21. The tocopherol cyclase according to claim 19, wherein the amino acid sequence fragment is -Xaa-Xaa-Ala-Val-Tyr-Val-Ala-Gln-Leu-Arg-Gly-Ile-Gly-Lys-(SEQ ID NO: 11).

22. The tocopherol cyclase according to claim 19, wherein the amino acid sequence fragment is -Gly-Ala-Gly-Leu-Ala-Arg-Phe-Glu-(SEQ ID NO: 12).

23. The tocopherol cyclase according to claim 19, wherein the amino acid sequence fragment is -Xaa-Asn-Ala-Leu-Tyr-Leu-Ile-Asp-Leu-Gln-Tyr-Thr-Gly-Gly-Gly-Xaa-Val-Lys-(SEQ ID NO: 13).

24. The tocopherol cyclase according to claim 19, wherein the amino acid sequence fragment is -Gln-Val-Pro-Arg-Glu-Ala-Asn-Asn-(SEQ ID NO: 14).

25. The tocopherol cyclase according to claim 19, wherein the amino acid sequence fragment is -Xaa-Leu-Ala-Pro-Val-Gln-Ser-Pro-(SEQ ID NO: 15).

26. The tocopherol cyclase according to claim 19, wherein the amino acid sequence fragment is -Gly-Leu-Asp-Leu-Ala-Pro-(SEQ ID NO: 16).

27. The tocopherol cyclase according to claim 19, wherein the amino acid sequence fragment is -Xaa-Val-Gln-Leu-Asp-Ser-Asp-Gly-Glu-Thr-Val-(SEQ ID NO: 17).

28. The tocopherol cyclase according to claim 19, wherein the amino acid sequence fragment is -Xaa-Leu-Pro-Val-(SEQ ID NO: 18).

29. The tocopherol cyclase according to claim 19 wherein the tocopherol cyclase enantioselectively produces R',R',R'-γ-tocopherol.

30. The tocopherol cyclase according to claim 19 isolated from soluble extract of *Chlorella protothecoides* or *Dunaliella salina*.

* * * * *

UNITED STATES PATENT AND TRADEMARK OFFICE
CERTIFICATE OF CORRECTION

PATENT NO. : 5,432,069
DATED : July 11, 1995
INVENTOR(S) : Fiona Gruninger, Erich Hochuli, Peter Karl Matzinger It is certified that error appears in the above-indentified patent and that said Letters Patent is hereby corrected as shown below:

In claim 3, column 21, line 36, delete "fractions" and insert -- extract --.

In claim 4, column 21, line 38, between "from" and "Chlorella" delete -- a --.

In claim 4, column 21, line 61, after "-Xaa-Leu-Pro-Val-(SEQ ID NO: 18)" insert -- , and --.

In claim 16, column 22, line 43, after "50 kD" insert -- , --.

In claim 30, column 24, line 32, between "from" and "soluble" insert -- a --.

Signed and Sealed this

Seventh Day of November, 1995

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

Ser Leu Tyr Asp Pro His Val Pro Xaa Met Tyr Asp Pro Ala Phe Xaa
    1              5                     10                     15

Xaa ( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Chlorella protothecoides ( x i ) SEQUENCE DESCRIPTION: SEQ ID NO:2:

Xaa Xaa Xaa Val Tyr Val Ala Gln Leu Xaa Gly Ile Gly Xaa
1               5                   10

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Chlorella protothecoides ( x i ) SEQUENCE DESCRIPTION: SEQ ID NO:3:

Xaa Ala Xaa Leu Ala Xaa Phe Glu
1               5

( 2 ) INFORMATION FOR SEQ ID NO:4:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Chlorella protothecoides ( x i ) SEQUENCE DESCRIPTION: SEQ ID NO:4:

Xaa Asn Ala Leu Tyr Leu Ile Asp Leu Gln Tyr Thr Xaa Gly Xaa Xaa
1               5                   10                  15

Val Lys ( 2 ) INFORMATION FOR SEQ ID NO:5:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Chlorella protothecoides ( x i ) SEQUENCE DESCRIPTION: SEQ ID NO:5:

Gln Val Pro Xaa Glu Ala Asn Asn
1               5

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Chlorella protothecoides (xi) SEQUENCE DESCRIPTION: SEQ ID NO:6:

```
Xaa Leu Ala Pro Val Gln Xaa Pro
 1               5
```

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Chlorella protothecoides (xi) SEQUENCE DESCRIPTION: SEQ ID NO:7:

```
Xaa Leu Asp Leu Ala Pro
 1               5
```

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Chlorella protothecoides (xi) SEQUENCE DESCRIPTION: SEQ ID NO:8:

```
Xaa Val Gln Leu Xaa Xaa Asp Gly Glu Xaa Val
 1               5                   10
```

(2) INFORMATION FOR SEQ ID NO:9:

(i) SEQUENCE CHARACTERISTICS:
        (A) LENGTH: 4 amino acids
        (B) TYPE: amino acid (C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
    (A) ORGANISM: Chlorella protothecoides (xi) SEQUENCE DESCRIPTION: SEQ ID NO:9:

```
Xaa  Leu  Xaa  Val
 1
```

(2) INFORMATION FOR SEQ ID NO:10:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Chlorella protothecoides (xi) SEQUENCE DESCRIPTION: SEQ ID NO:10:

```
Ser  Leu  Tyr  Asp  Pro  His  Val  Pro  Thr  Met  Tyr  Asp  Pro  Ala  Phe  Arg
 1                   5                        10                        15
Thr
```

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Chlorella protothecoides (xi) SEQUENCE DESCRIPTION: SEQ ID NO:11:

```
Xaa  Xaa  Ala  Val  Tyr  Val  Ala  Gln  Leu  Arg  Gly  Ile  Gly  Lys
 1                   5                        10
```

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (i i i) HYPOTHETICAL: NO (i v) ANTI-SENSE: NO (v) FRAGMENT TYPE: internal (v i) ORIGINAL SOURCE:
    (A) ORGANISM: Chlorella protothecoides (x i) SEQUENCE DESCRIPTION: SEQ ID NO:12:

```
Gly Ala Gly Leu Ala Arg Phe Glu
1               5
```

(2) INFORMATION FOR SEQ ID NO:13:

(i) SEQUENCE CHARACTERISTICS:
    (A) LENGTH: 18 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
    (A) ORGANISM: Chlorella protothecoides (x i) SEQUENCE DESCRIPTION: SEQ ID NO:13:

```
Xaa Asn Ala Leu Tyr Leu Ile Asp Leu Gln Tyr Thr Gly Gly Gly Xaa
1               5                   10                  15
Val Lys
```

(2) INFORMATION FOR SEQ ID NO:14:

(i) SEQUENCE CHARACTERISTICS:
    (A) LENGTH: 8 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (v i) ORIGINAL SOURCE:
    (A) ORGANISM: Chlorella protothecoides (x i) SEQUENCE DESCRIPTION: SEQ ID NO:14:

```
Gln Val Pro Arg Glu Ala Asn Asn
1               5
```

(2) INFORMATION FOR SEQ ID NO:15:

(i) SEQUENCE CHARACTERISTICS:
    (A) LENGTH: 8 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v) FRAGMENT TYPE: internal (vi) ORIGINAL SOURCE:
    (A) ORGANISM: Chlorella protothecoides (xi) SEQUENCE DESCRIPTION: SEQ ID NO:15:

Xaa Leu Ala Pro Val Gln Ser Pro
1               5

(2) INFORMATION FOR SEQ ID NO:16:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
       (A) ORGANISM: Chlorella protothecoides (xi) SEQUENCE DESCRIPTION: SEQ ID NO:16:

Gly Leu Asp Leu Ala Pro
1               5

(2) INFORMATION FOR SEQ ID NO:17:

(i) SEQUENCE CHARACTERISTICS:
       (A) LENGTH: 11 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
       (A) ORGANISM: Chlorella protothecoides (xi) SEQUENCE DESCRIPTION: SEQ ID NO:17:

Xaa Val Gln Leu Asp Ser Asp Gly Glu Thr Val
1               5                   10

(2) INFORMATION FOR SEQ ID NO:18:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
       (A) ORGANISM: Chlorella protothecoides (xi) SEQUENCE DESCRIPTION: SEQ ID NO:18:

Xaa Leu Pro Val